(12) United States Patent
Wang et al.

(10) Patent No.: US 8,917,354 B2
(45) Date of Patent: Dec. 23, 2014

(54) MOTION DETECTION IN VIDEO FIELDS

(71) Applicant: Amlogic Co., Ltd., Santa Clara, CA (US)

(72) Inventors: Dongjian Wang, San Jose, CA (US); Xin Hu, Shanghai (CN); Xuyun Chen, San Jose, CA (US)

(73) Assignee: Amlogic Co., Ltd., Santa Clara, CA (US)

( * ) Notice: Subject to any disclaimer, the term of this patent is extended or adjusted under 35 U.S.C. 154(b) by 64 days.

(21) Appl. No.: 14/042,601

(22) Filed: Sep. 30, 2013

(65) Prior Publication Data

US 2014/0085536 A1 Mar. 27, 2014

(51) Int. Cl.
*H04N 7/01* (2006.01)
*H04N 11/20* (2006.01)
*A61F 2/46* (2006.01)
*A61F 2/44* (2006.01)
*A61F 2/30* (2006.01)
*A61F 2/28* (2006.01)

(52) U.S. Cl.
CPC .............. *H04N 7/014* (2013.01); *A61F 2/4684* (2013.01); *A61F 2002/30878* (2013.01); *A61F 2310/00011* (2013.01); *A61F 2310/00958* (2013.01); *A61F 2310/00796* (2013.01); *A61F 2/30744* (2013.01); *A61F 2002/2835* (2013.01); *A61F 2/4425* (2013.01); *A61F 2310/00131* (2013.01); *A61F 2310/00089* (2013.01); *A61F 2002/30013* (2013.01); *A61F 2002/30616* (2013.01); *A61F 2310/00359* (2013.01); *A61F 2002/30354* (2013.01); *A61F 2002/30428* (2013.01); *A61F 2002/30062* (2013.01); *A61F 2002/30596* (2013.01); *A61F 2310/00976* (2013.01); *A61F 2002/4475* (2013.01); *A61F 2310/00149* (2013.01); *A61F 2310/00023* (2013.01); *A61F 2002/30611* (2013.01); *A61F 2002/30515* (2013.01); *A61F 2310/00029* (2013.01); *A61F 2310/0097* (2013.01); *A61F 2310/00317* (2013.01); *A61F 2/4465* (2013.01); *A61F 2002/30784* (2013.01); *A61F 2310/00017* (2013.01); *A61F 2002/30092* (2013.01); *A61F 2002/30843* (2013.01); *A16F 2002/30785* (2013.01); *A61F 2310/00179* (2013.01); *A61F 2002/30393* (2013.01); *A61F 2002/30652* (2013.01); *A61F 2310/00203* (2013.01); *H04N 7/0145* (2013.01); *A61F 2310/00095* (2013.01); *A61F 2310/00293* (2013.01)
USPC ........... 348/452; 348/451; 348/453; 348/468; 348/474; 348/477; 348/446; 348/423.1; 348/429.1; 348/502; 348/503; 348/511; 348/513; 348/515; 348/516; 348/522; 348/567; 348/575; 348/609; 348/610; 348/663; 348/687; 348/739; 348/180; 348/128; 348/69; 345/582; 345/589; 345/606; 382/107; 382/162; 382/172; 382/236; 382/299

(58) Field of Classification Search
USPC ......... 348/452, 451, 453, 467, 468, 477, 446, 348/180, 167, 502, 503, 511, 513, 567, 609, 348/610, 663, 687, 423.1, 429.1, 474, 128, 348/69, 515, 516, 522, 575; 345/582, 589, 345/606; 382/162, 107, 236, 299, 172
See application file for complete search history.

(56) References Cited

U.S. PATENT DOCUMENTS 5,461,420 A * 10/1995 Yonemitsu et al. ...... 375/240.15
6,204,857 B1 * 3/2001 Piazza et al. .................. 345/582

(Continued)

*Primary Examiner* — Jefferey Harold
*Assistant Examiner* — Mustafizur Rahman
(74) *Attorney, Agent, or Firm* — Venture Pacific Law, PC

(57) ABSTRACT

A method for detecting motion in video fields of video data, comprises the steps of: calculating texture information for a pixel in the video fields; determining a threshold value as a function of the calculated texture information; calculating a differential value for the pixel; and detecting motion in the video fields as a function of the determined threshold value and the calculated differential value.

20 Claims, 4 Drawing Sheets

(56) References Cited

U.S. PATENT DOCUMENTS

| | | | |
|---|---|---|---|
| 6,330,344 B1* | 12/2001 | Kondo et al. | 382/107 |
| 6,639,598 B2* | 10/2003 | Piazza et al. | 345/428 |
| 7,151,863 B1* | 12/2006 | Bradley et al. | 382/299 |
| 7,477,761 B2* | 1/2009 | Kondo et al. | 382/107 |
| 7,701,508 B2* | 4/2010 | Wang et al. | 348/452 |
| 7,961,252 B2* | 6/2011 | Pai et al. | 348/448 |
| 8,135,215 B2* | 3/2012 | Kameyama | 382/167 |
| 8,543,894 B1* | 9/2013 | Varnica et al. | 714/794 |
| 2001/0020948 A1* | 9/2001 | Piazza et al. | 345/586 |
| 2004/0057602 A1* | 3/2004 | Kondo et al. | 382/107 |
| 2004/0196371 A1* | 10/2004 | Kono et al. | 348/162 |
| 2005/0128292 A1* | 6/2005 | Miyamaki et al. | 348/143 |
| 2005/0232356 A1* | 10/2005 | Gomi et al. | 375/240.16 |
| 2007/0121001 A1* | 5/2007 | Wang et al. | 348/452 |
| 2007/0229534 A1* | 10/2007 | Kim et al. | 345/606 |
| 2008/0094505 A1* | 4/2008 | Pai et al. | 348/452 |
| 2009/0190030 A1* | 7/2009 | Nix et al. | 348/452 |
| 2010/0134632 A1* | 6/2010 | Won et al. | 348/169 |
| 2010/0295991 A1* | 11/2010 | Yano et al. | 348/453 |
| 2011/0091103 A1* | 4/2011 | Kameyama | 382/167 |

* cited by examiner

MOTION DETECTION IN VIDEO FIELDS

FIELD OF INVENTION

This invention generally relates to video processing, and, in particular, to motion detection in video fields for deinterlacing of the video fields for display.

BACKGROUND

Video frames are typically encoded in an interlaced format comprising a first video field (e.g., a top video field) and a second video field (e.g., a bottom video field), each video field having alternating lines of the video frame and each field being temporally separated. Video images are typically encoded and transmitted to a receiver in such an interlaced format as a compromise between bandwidth and video image resolution. Since interlaced video frames are displayed using only half the lines of a full video frame, less system bandwidth is required to process and display these video frames. However, since the human eye typically cannot resolve a single video field, but rather, blends the first field and the second field, the perceived image has the vertical resolution of both fields combined.

Some types of receivers, including computers, televisions, mobile phones, computing tablets, etc., may require the use of de-interlaced video frames instead of interlaced video frames. For such receivers, the video frames encoded in an interlaced format must be de-interlaced prior to display. Typically, any missing pixels from the video frame are interpolated using the pixels of the first video field and the second video field.

There are several well-known methods to construct de-interlaced video frames. One such method is commonly referred to as the "bob" method in which a de-interlaced video frame is constructed from a single video field that is vertically interpolated. Whether to rely on a spatial or a temporal interpolation to interpolate an image data is decided by detecting the motion of a subject in the picture. Specifically, spatial interpolation is used to interpolate image data for pixels that are sensing a subject in motion, and temporal interpolation is used to interpolate image data for pixels that are sensing a motionless subject. In this way, by switching interpolation methods according to the state of motion of the subject being sensed by individual pixels, it is possible to faithfully reproduce the sensed subject in each field of the picture being played back.

Conventionally, such detection of motion is achieved by calculating differences of the image data of identical pixels among even-numbered and odd-numbered fields, and then comparing those differences with a predetermined threshold value. If the differences are greater than the threshold value, the subject being sensed by the pixels in question is recognized to be in motion.

In this way, by comparing the field-to-field differences of the image data of identical pixels with a constant, predefined threshold value, whether the subject being sensed by the pixels for which image data is going to be interpolated is in motion or not is judged. However, as long as such a threshold level is kept constant, for example, in a case where motion was present up to the field immediately previous to the one currently being reproduced but no motion is present any more in the current field, the motion that had been recognized just up to the previous field leads to an erroneous judgment that the motion is still present in the current field. In addition, the predefined threshold value has no relationship between any of the other pixels in the current video field/frame, which can lead to inaccurate results during interpolation.

This makes faithful reproduction of the real image impossible, and sometimes causes flickering or the like while a motion picture is being played back. Therefore, it would be desirable to provide new methods and systems for motion detection in video fields that can use an adaptive threshold value, conserve processing power, and increase system bandwidth.

SUMMARY OF INVENTION

An object of this invention is to provide methods and systems for motion detection in video fields that are adaptive to texture information and combing information of the video fields.

Another object of this invention is to provide methods and systems for motion detection in video fields that minimize the use of memory.

Yet another object of this invention is to provide methods and systems for motion detection in video fields that can be used for deinterlacing.

Briefly, the present invention discloses methods and systems for detecting motion in video fields of video data, comprising the steps of: calculating texture information for a pixel in the video fields; determining a threshold value as a function of the calculated texture information; calculating a differential value for the pixel; and detecting motion in the video fields as a function of the determined threshold value and the calculated differential value.

An advantage of this invention is that methods and systems for motion detection in video fields are provided that are adaptive to texture information and combing information of the video fields.

Another advantage of this invention is that methods and systems for motion detection in video fields are provided that minimize the use of memory.

Yet another advantage of this invention is that methods and systems for motion detection in video fields that can be used for deinterlacing.

DESCRIPTION OF THE DRAWINGS

The foregoing and other objects, aspects, and advantages of the invention can be better understood from the following detailed description of the preferred embodiment of the invention when taken in conjunction with the accompanying drawings.

DETAILED DESCRIPTION OF THE PREFERRED EMBODIMENTS

In the following detailed description of the embodiments, reference is made to the accompanying drawings, which form a part hereof, and in which is shown by way of illustration of specific embodiments in which the present invention may be practiced.

Figure 1:
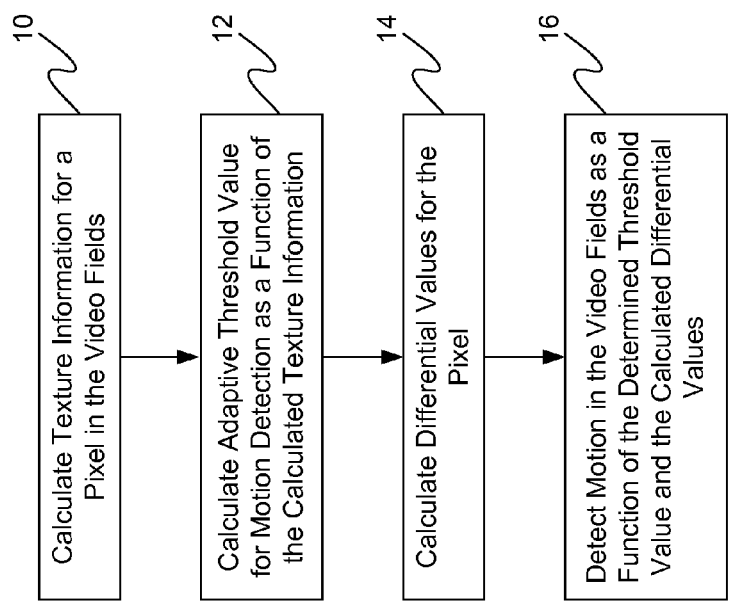
FIG. 1 illustrates a flow chart of the present invention for motion detection in video fields.

FIG. 1 illustrates a flow chart of the present invention for motion detection in video fields. In a video stream, multiple video fields can be decoded for display. Motion detection can be used to improve performance in decoding of the video fields.

Texture information can be calculated 10 for a pixel in the video fields to detect motion for the pixel. For instance, texture information can include a vertical infield texture value txt1 and a horizontal intra-field texture value txt3. The vertical infield texture value txt1 can be calculated for a pixel having a position (x,y) in a current video field at time t by applying a low pass filter ("lpf") to an absolute difference in luma values f(a,b,c) of neighboring vertical pixels (i.e., pixels at (x, y−1) and (x, y+1) in a previous field (i.e., time=t−1). The following equation can be used to calculate txt1:

$$\text{txt1}(y,x,t-1)=\text{lpf}^*|f(y-1,x,t-1)-f(y+1,x,t-1)| \quad \text{Equation [1]}$$

The horizontal intra-field texture value txt3 can be calculated for the pixel having position (x,y) in the current video field at the time t by applying a min, max, or average function G(d,e,f) on the difference of textures in different video fields. Each texture txt is based on a single video field, where the video fields can be of the same polarity. Same polarity can mean that the two video fields are both in top fields or both in bottom fields. The texture txt3 can be calculated using the following equation:

$$\text{txt3}(y,x,t-1)=G(\text{txt}(y,x,t),\text{txt}(y,x,t-2)|) \quad \text{Equation [2]}$$

where $\text{txt}(a,b,c)=\text{lpf}^*G(|f(a-2,b,c)-f(a,b,c)|,|f(a+2,b,c)-f(a,b,c)|)$.

An adaptive threshold thd can be calculated for motion detection 21 as a function of the calculated texture information. For instance, the adaptive threshold can equal:

$$\text{thd}=\alpha^*\text{txt1}+\beta^*\text{txt3} \quad \text{Equation [3]}$$

where $\alpha$ and $\beta$ are predefined constants. The predefined constants $\alpha$ and $\beta$ can be determined based upon empirical and/or statistical analysis. For instance, $\alpha$ can be set to 0.3 and $\beta$ can be set to 0.5 for luma components.

In addition, differential values for the pixel can be calculated 14 for the pixel in the various video fields. The differential value for the pixel is calculated based on the difference of the luma values f(a,b,c) for that pixel position in two or more video fields. Alternatively, chroma values for the pixel position can be used, as well as other video characteristics for the pixel position. Typically, the difference in luma values can be based on the luma value in the current field (e.g., time=t) and the luma value in the previous field that has the same polarity as the current field (e.g., two fields away, time=t−2). This differential value can be referred to as $\text{Dif}_{02}$ for the pixel, which can equal:

$$\text{Dif}_{02}(y,x,t,t-1)=f(y,x,t)-f(y,x,t-2) \quad \text{Equation [4]}$$

Additionally other differential values can be calculated depending on the number of video fields used to detect motion for a particular pixel of the current video field. In the current example, there are a total of three video fields, including the current video field, the previous field, and the previous, previous video field. Thus, the other differentials can equal:

$$\text{Dif}_{01}(y,x,t,t-1)=f(y,x,t)-f(y,x,t-1) \quad \text{Equation [5]}$$

$$\text{Dif}_{21}(y,x,t-2,t-1)=f(y,x,t-2)-f_i(y,x,t-1) \quad \text{Equation [6]}$$

where $f_i(a,b,c)$ is an interpolated value for the pixel at the given time. The other differentials $\text{Dif}_{01}$ and $\text{Dif}_{21}$ can also be used for determining an adaptive combing value (not shown in the flow chart, but illustrated in FIG. 4).

Motion detection can be determined for the pixel in the video fields 16 as a function of the determined threshold 12 and the calculated differential values 14. For instance, the differential value $\text{Dif}_{02}$ and the adaptive threshold are compared to determine whether motion is detected for the respective pixel. If the differential value $\text{Dif}_{02}$ is greater than the adaptive threshold, then motion is detected for the pixel; else, motion is not detected for the pixel.

Figure 2:
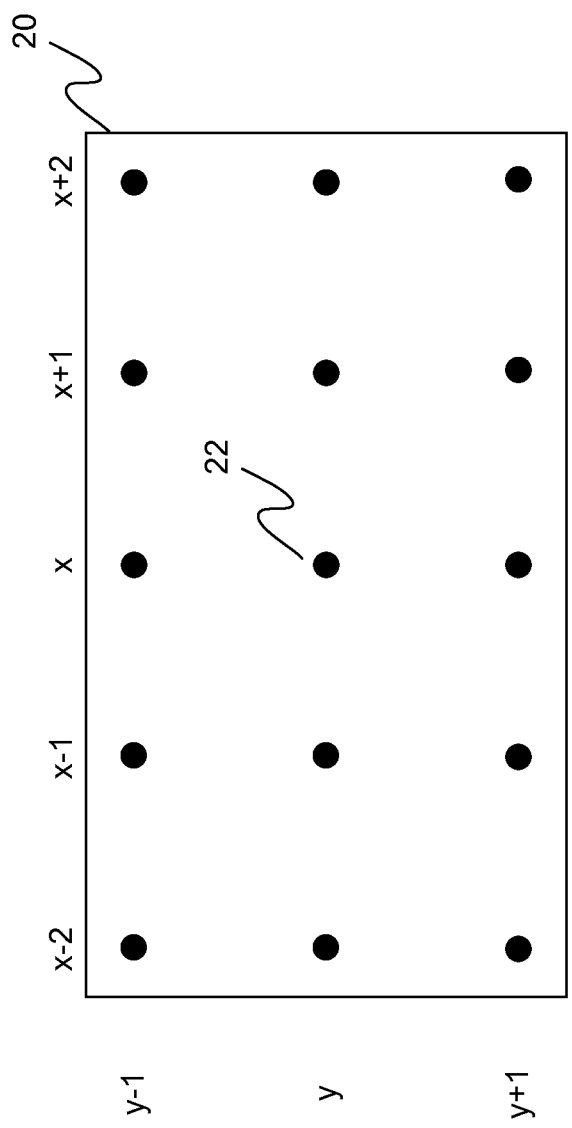
FIG. 2 illustrates a video field at a predefined time.

FIG. 2 illustrates a video field at a predefined time. A video field 20 of a video stream can comprise pixels in an array format of rows and columns. The video field 20 can comprise a pixel location 22 at row y and column x. The methods and systems of the present invention can be used to generate a one bit motion flag for each pixel in the video field 20, and in particular for the pixel location 22.

Figure 3:
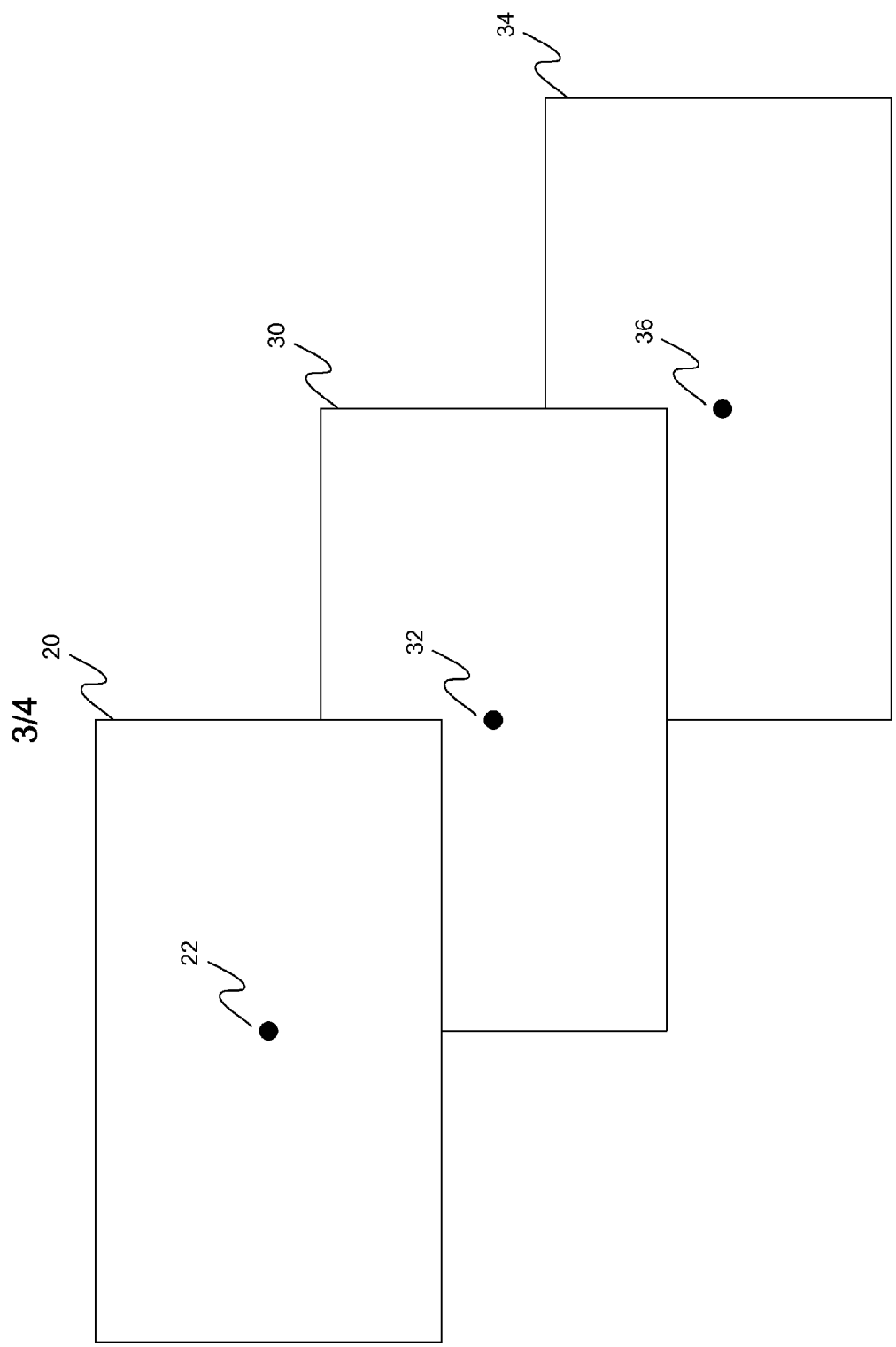
FIG. 3 illustrates various video fields.

FIG. 3 illustrates various video fields at various times. The video field 20 of the video stream can be at time t. A video field 30 of the video stream can be at time t−1, and be the previous field from the video field 20. A video field 34 can be at time t−2 and be two previous fields from the video field 20. The pixel location 22 can be at row y and column x in video field 20. A pixel location 32 can be at row y and column x in video field 30. The pixel location 36 can be at row y and column x in video field 34. The methods and systems of the present invention can use multiple video fields to generate one bit motion values for each pixel in the video fields for decoding of the video fields.

Figure 4:
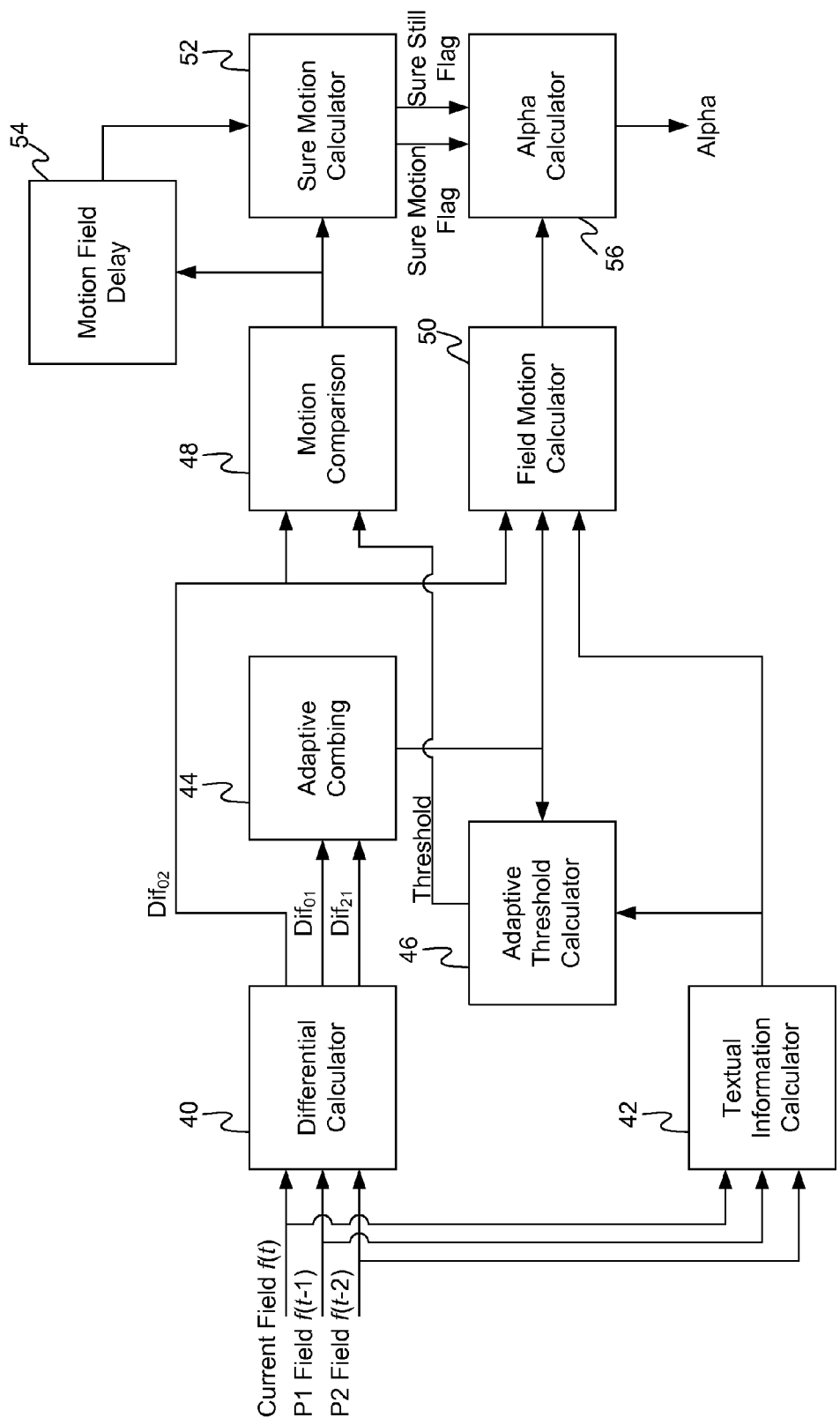
FIG. 4 illustrates a block diagram of the present invention for motion detection in video fields.

FIG. 4 illustrates a block diagram of the present invention for motion detection in video fields. A motion detector of the present invention comprises a differential calculator 40, a textual information calculator 42, an adaptive combing block 44, an adaptive threshold calculator 46, a motion comparison block 48, a field motion calculator 50, a sure motion calculator 52, a motion field delay block 54, and an alpha calculator 56.

The luma functions for a current field f(t), a first previous field f(t−1), and a second previous field f(t−2) are inputted to the differential calculator 40. The differential calculator calculates various differential values for a pixel position in the various fields, including the differential values $\text{Dif}_{02}$, $\text{Dif}_{01}$, and $\text{Dif}_{21}$. The differential values $\text{Dif}_{01}$ and $\text{Dif}_{21}$ are inputted to the adaptive combing block 44 for determining an adaptive combing value cmb. The adaptive combing value can be equal to the following:

$$\text{cmb}=G(\text{Dif}(x,y,t\,t-1),\text{Dif}(x,y,t,t-2)) \quad \text{Equation (7)}$$

The differential value $\text{Dif}_{02}$ is inputted to the motion comparison block 48 and the field motion calculator 50.

The luma functions for the current field f(t), the first previous field f(t−1), and the second previous field f(t−2) are also inputted to the textual information calculator 42. The textual information calculator 42 determines textural information for the video fields, including txt1 and txt3. The determined textural information is inputted to the adaptive threshold calculator 46 and the field motion calculator 50.

The adaptive threshold calculator 46 receives the textual information and the combing value cmb, and calculates an adaptive threshold. The adaptive threshold can be updated as needed or required. For instance, the threshold result of Equation [3] can be compared with a scaled combing value. The larger of two values can be selected as a new adaptive threshold value.

The adaptive threshold is outputted to the motion comparison block 48. The motion comparison block 48 compares the differential value $\text{Dif}_{02}$ and the adaptive threshold to detect motion for the respective pixel. The motion comparison block 48 can output a one-bit motion value (e.g., the motion value can be as follows mot(x,y,t)) to indicate whether a motion has been detected for the respective pixel. For instance, a 0 motion value can indicate that there is no motion detected for the pixel, and a 1 motion value can indicate that motion is detected for the pixel. Thus, the motion value is equal to zero when the $Dif_{o2}$ is greater than the adaptive threshold; and the motion value is equal to one for any other cases. Next, the motion value can be stored by the motion field delay 54, and inputted to the sure motion calculator 52.

The motion field delay 54 can store a motion value for each of the pixels of the current field and other fields. A motion history ("hist") can be stored as the following equation:

hist(y,x,t)=L(hist,mot), Equation [8]

where hist is an iterative function for indicating the motion/static history of a video field. For instance, assume hist(y,x,t−2)=[mot(y,x,t−8),mot(y,x,t−6),mot(y,x,t−4),mot(y,x,t−2)], then hist(y,x,t) can comprise 4-bits for each pixel since hist(y,x,t)=L(hist(y,x,t−2), mot(y,x,t)), where L is a function operator for the various motion values.

The motion values and hist can be read, and then used by the sure motion calculator 52 to confirm that motion is being detected for the current field (i.e., mot(y,x,t)) and/or other fields (e.g., from the motion field delay 54, including hist(y,x,t−2), hist(y−1,x,t−1) and hist(y+1,x,t−1)). If motion is confirmed, then the sure motion calculator 52 can send a sure motion flag to the alpha calculator 56. If motion is not confirmed, then the sure motion calculator 52 can send a still motion flag to the alpha calculator 56.

The field motion calculator 50 can receive the differential value $Dif_{o2}$, the adaptive combing cmb and the textual information for generating a field motion value for use by the alpha calculator 56. The field motion calculator 50 calculates a quantified field motion ("fMt0") between the current video field (time=t) and the previous, previous video field (time=t−2), which can equal:

fMt0=|Dif(y,x,t,t−2)|−H(I(txt1,txt3),cmb), Equation [9]

where H(k,l)=a1\*k+a2\*l+a3 and I(m,n)=b1\*m+b2\*n+b3. The values a1, a2, a3, b1, b2, and b3 can be predefined and can be implemented by programmable registers.

The field motion calculator 50 also calculates a quantified field motion ("fMt1") between the previous, previous video field (time=t−2) and the previous video field (time=t−1), which can equal:

fMt1=|dif(y,x,t−1,t−2)|K(I(txt1,txt3),cmb), Equation [10]

where K(k,l)=a1\*k+a2\*l+a3.

The alpha calculator 56 uses the field motion calculator and the motion flags to determine an alpha for use by a blender during the decoding of the respective fields. Alpha can equal the following:

alpha=M(fMt0,mot,pSM,pSS), Equation[11]

where pSM is the sure motion flag, pSS is the sure still flag, and M(a,b,c,d) function is as follows:

if pSM(y,x,t−1) is true, then there is motion and alpha=a maximum value (e.g. 15 for 4-bit value);

if pSS(y,x,t−1) is true, there there is no motion and is static, thus alpha=a minimum value (e.g. 0); and otherwise, alpha is scaled as a function of the fMt0 and mot.

While the present invention has been described with reference to certain preferred embodiments or methods, it is to be understood that the present invention is not limited to such specific embodiments or methods. Rather, it is the inventor's contention that the invention be understood and construed in its broadest meaning as reflected by the following claims. Thus, these claims are to be understood as incorporating not only the preferred apparatuses, methods, and systems described herein, but all those other and further alterations and modifications as would be apparent to those of ordinary skilled in the art.

We claim:

1. A method for detecting motion in video fields of video data, comprising the steps of:
    calculating texture information for a pixel in the video fields;
    determining a threshold value as a function of the calculated texture information;
    calculating differential values for the pixel as a function of certain ones of the video fields; and
    detecting motion in the video fields as a function of the determined threshold value and the calculated differential values.

2. The method of claim 1 wherein motion is detected for the pixel when a certain one of the calculated differential values is greater than the determined threshold value.

3. The method of claim 1 wherein the texture information comprises a vertical infield texture value and a horizontal intra-field texture value.

4. The method of claim 3 wherein the determined threshold value is equal to thd=$\alpha$\*txt1+$\beta$\*txt3, where alpha and beta are predefined constants, where txt1 is the vertical infield texture value and the txt3 is the horizontal intra-field texture value.

5. The method of claim 3 wherein the pixel location has a vertical position y, a horizontal position x, and is in a current field at time ("t"), and wherein the vertical infield texture value is equal to txt1(y,x,t−1)=lpf\*|f(y−1,x,t−1)−f(y+1,x,t−1)|, where f(a,b,c) is the luminance function for a field at row a, column b, and time c and lpf is a low pass filter.

6. The method of claim 3 wherein the pixel location has a vertical position y, a horizontal position x, and is in a current field at time ("t"), and wherein the horizontal intra-field texture value is equal to txt3(y,x,t−1)=G(txt(y,x,t), txt(y,x,t−2)|), where txt(a,b,c)=lpf\*G(|f(a−2,b,c)−f(a,b,c)|, |f(a+2,b,c)−f(a,b,c)|) and f(a,b,c) is the luminance function for a field at row a, column b, and time c and lpf is a low pass filter.

7. The method of claim 1 wherein the detected motion for the pixel is indicated by storing a one bit flag for the pixel location.

8. The method of claim 7 wherein an array of one bit flags are generated for pixels of a certain one of the video fields and wherein the array of one bit flags is read during deinterlacing of the video fields.

9. The method of claim 1 in the calculating the differential values step, wherein a first differential value is calculated for the pixel as a function of the pixel in a current field and of the pixel in a second previous field.

10. The method of claim 1 wherein a second differential value is calculated for the pixel as a function of the pixel in a current field and of the pixel in a first previous field and wherein a third differential value is calculated for the pixel as a function of the pixel in a second previous field and of the pixel in the first previous field.

11. The method of claim 10 wherein an adaptive combing value is calculated as a function of the second differential value and the third differential value, and wherein the adaptive combing value is used to update the threshold value.

12. The method of claim 11 wherein a first quantified field motion is calculated as a function of the calculated differential values, the calculated texture information, and the adaptive combing value.

13. The method of claim 12 wherein a second quantified field motion is calculated as a function of the third differential value and the calculated texture information.

14. The method of claim 13 wherein an alpha value for blending is calculated as a function of the first quantified field motion, the second quantified field motion, the detected motion, and a motion history.

15. A method for detecting motion in video fields of video data, comprising the steps of:
   calculating texture information for a pixel in the video fields, wherein the texture information comprises a vertical infield texture value and a horizontal intra-field texture value;
   determining a threshold value as a function of the calculated texture information;
   calculating a differential value for the pixel; and
   detecting motion in the video fields as a function of the determined threshold value and the calculated differential value,
   wherein motion is detected for the pixel when the calculated differential value is greater than the determined threshold value,
   wherein the detected motion for the pixel is indicated by storing a one bit flag for the pixel location, and
   wherein an array of one bit flags are generated for pixels of a certain one of the video fields and wherein the array of one bit flags is read during deinterlacing of the video fields.

16. The method of claim 15 wherein the determined threshold value is equal to thd=$\alpha$*txt1+$\beta$*txt3, where alpha and beta are predefined constants, where txt1 is the vertical infield texture value and the txt3 is the horizontal intra-field texture value, wherein the pixel location has a vertical position y, a horizontal position x, and is in a current field at time ("t"), and wherein the vertical infield texture value is equal to txt1(y,x,t−1)=lpf*|f(y−1,x,t−1)−f(y+1,x,t−1)|, where f(a,b,c) is the luminance function for a field at row a, column b, and time c and lpf is a low pass filter.

17. The method of claim 15 wherein the pixel location has a vertical position y, a horizontal position x, and is in a current field at time ("t"), and wherein the horizontal intra-field texture value is equal to txt3(y,x,t−1)=G(txt(y,x,t), txt(y,x,t−2)|), where txt(a,b,c)=lpf*G(|f(a−2,b,c)−f(a,b,c)|, |f(a+2,b,c)−f(a,b,c)|) and f(a,b,c) is the luminance function for a field at row a, column b, and time c and lpf is a low pass filter.

18. The method of claim 15 wherein the calculated differential value for the pixel is a function of the pixel in a current field and of the pixel in a second previous field, wherein a second differential value is calculated for the pixel as a function of the pixel in a current field and of the pixel in a first previous field, wherein a third differential value is calculated for the pixel as a function of the pixel in a second previous field and of the pixel in the first previous field, wherein an adaptive combing value is calculated as a function of the second differential value and the third differential value, wherein the adaptive combing value is used to update the threshold value, wherein a first quantified field motion is calculated as a function of the calculated differential value, the calculated texture information, and the adaptive combing value, wherein a second quantified field motion is calculated as a function of the third differential value and the calculated texture information, and wherein an alpha value for blending is calculated as a function of the first quantified field motion, the second quantified field motion, the detected motion, and a motion history.

19. A method for detecting motion in video fields of video data, comprising the steps of:
   calculating texture information for a pixel in the video fields, wherein the texture information comprises a vertical infield texture value and a horizontal intra-field texture value, wherein the pixel location has a vertical position y, a horizontal position x, and is in a current field at time ("t"), and wherein the vertical infield texture value is equal to txt1(y,x,t−1)=lpf*|f(y−1,x,t−1)−f(y+1,x,t−1)|, wherein the horizontal intra-field texture value is equal to txt3(y,x,t−1)=G(txt(y,x,t), txt(y,x,t−2)|), where txt(a,b,c)=lpf*G(|f(a−2,b,c)−f(a,b,c)|, If (a+2,b,c)−f(a,b,c)|), where f(a,b,c) is the luminance function for a field at row a, column b, and time c and lpf is a low pass filter;
   determining a threshold value as a function of the calculated texture information, wherein the determined threshold value is equal to thd=$\alpha$*txt1+$\beta$*txt3, where alpha and beta are predefined constants, where txt1 is the vertical infield texture value and the txt3 is the horizontal intra-field texture value;
   calculating a differential value for the pixel; and
   detecting motion in the video fields as a function of the determined threshold value and the calculated differential value,
   wherein motion is detected for the pixel when the calculated differential value is greater than the determined threshold value,
   wherein the detected motion for the pixel is indicated by storing a one bit flag for the pixel location, and
   wherein an array of one bit flags are generated for pixels of a certain one of the video fields and wherein the array of one bit flags is read during deinterlacing of the video fields.

20. The method of claim 19 wherein the calculated differential value for the pixel is a function of the pixel in a current field and of the pixel in a second previous field, wherein a second differential value is calculated for the pixel as a function of the pixel in a current field and of the pixel in a first previous field, wherein a third differential value is calculated for the pixel as a function of the pixel in a second previous field and of the pixel in the first previous field, wherein an adaptive combing value is calculated as a function of the second differential value and the third differential value, wherein the adaptive combing value is used to update the threshold value, wherein a first quantified field motion is calculated as a function of the calculated differential value, the calculated texture information, and the adaptive combing value, wherein a second quantified field motion is calculated as a function of the third differential value and the calculated texture information, and wherein an alpha value for blending is calculated as a function of the first quantified field motion, the second quantified field motion, the detected motion, and a motion history.

* * * * *